(12) United States Patent
Saiki

(10) Patent No.: US 7,456,307 B2
(45) Date of Patent: Nov. 25, 2008

(54) PREPARATION OF A HALOSILYLATED CHAIN HYDROCARBON

(75) Inventor: Takeaki Saiki, Ichihara (JP)

(73) Assignee: Dow Corning Toray Company, Ltd., Tokyo (JP)

( * ) Notice: Subject to any disclaimer, the term of this patent is extended or adjusted under 35 U.S.C. 154(b) by 5 days.

(21) Appl. No.: 10/573,792

(22) PCT Filed: Oct. 1, 2004

(86) PCT No.: PCT/JP2004/014908

§ 371 (c)(1),
(2), (4) Date: Nov. 6, 2006

(87) PCT Pub. No.: WO2005/033116

PCT Pub. Date: Apr. 14, 2005

(65) Prior Publication Data

US 2007/0055074 A1    Mar. 8, 2007

(30) Foreign Application Priority Data

Oct. 2, 2003  (JP) ............................. 2003-344602

(51) Int. Cl.
*C07F 7/04* (2006.01)
(52) U.S. Cl. ..................................................... 556/467
(58) Field of Classification Search ........................ None
See application file for complete search history.

(56) References Cited

U.S. PATENT DOCUMENTS

| | | | |
|---|---|---|---|
| 4,820,674 A * | 4/1989 | Shiozawa et al. ........... 502/169 |
| 5,359,111 A | 10/1994 | Kleyer et al. | |
| 5,424,470 A | 6/1995 | Bank et al. | |
| 5,449,802 A | 9/1995 | Bank et al. | |
| 5,486,637 A | 1/1996 | Bank et al. | |
| 5,493,045 A | 2/1996 | Bank et al. | |
| 5,623,083 A | 4/1997 | Bank et al. | |

FOREIGN PATENT DOCUMENTS

| | | |
|---|---|---|
| EP | 0533170 A1 | 3/1993 |
| EP | 0589613 A1 | 3/1994 |
| EP | 0602922 A1 | 6/1994 |
| JP | 5213972 | 8/1993 |
| JP | 6234777 | 8/1994 |
| JP | 8208838 | 8/1996 |
| JP | 8231563 | 9/1996 |
| JP | 8291181 | 11/1996 |
| JP | 9025281 | 1/1997 |
| JP | 9157276 | 6/1997 |
| JP | 9192494 | 7/1997 |
| JP | 10029996 | 2/1998 |
| JP | 11080167 | 3/1999 |

OTHER PUBLICATIONS

English language abstract for JP5213972 extracted from esp@cenet database, Aug. 10, 2006.
English language abstract for JP6234777 extracted from esp@cenet database, Aug. 10, 2006.
English language abstract for JP82088382 extracted from esp@cenet database, Aug. 10, 2006.
English language abstract for JP8231563 extracted from esp@cenet database, Aug. 10, 2006.
English language abstract for JP8291181 extracted from esp@cenet database, Aug. 10, 2006.
English language abstract for JP9025281 extracted from esp@cenet database, Nov. 3, 2006.
English language abstract for JP9157276 extracted from esp @cenet database, Aug. 10, 2006.
English language abstract for JP9192494 extracted from esp@cenet database, Aug. 10, 2006.
English language abstract for JP10029996 extracted from esp@cenet database, Nov. 3, 2006.
English language abstract for JP11080167 extracted from esp@cenet database, Nov. 3, 2006.

* cited by examiner

*Primary Examiner*—Samuel A Barts
(74) *Attorney, Agent, or Firm*—Howard & Howard Attorneys, P.C.

(57) ABSTRACT

A method for the preparation of a chain hydrocarbon halosilylated at its terminal carbon atom or terminal carbon atoms by subjecting a diene-type compound and a hydrogenhalosilane to a hydrosilylation reaction in the presence of a hydrosilylation catalyst and an ether compound having no aliphatic triple bond. A method of conducting a hydrosilylation reaction between a diene-type compound that has vinyl groups on both terminals and a hydrogenhalosilane in the presence of a hydrosilylation catalyst and an ether compound having no aliphatic triple bond.

10 Claims, No Drawings

PREPARATION OF A HALOSILYLATED CHAIN HYDROCARBON

RELATED APPLICATIONS

This application claims priority to and all the advantages of International Application No. PCT/US2004/014908, filed on Oct. 1, 2004, which claims priority to Japanese Patent Application No. 2003-344602, filed on Oct. 2, 2003.

TECHNICAL FIELD

The present invention relates to a method for the preparation of a chain hydrocarbon halosilylated at its terminal carbon atom or terminal carbon atoms and a method of conducting a hydrosilylation reaction between a diene-type compound that has vinyl groups on both terminals and a hydrogenhalsilane.

BACKGROUND ART

A hydrosilylation reaction that combines a compound with a vinyl group and a compound with a silicon-bonded hydrogen atom by reacting them in the presence of a platinum catalyst is a reaction that is commonly used in the synthesis of organosilanes and organopolysiloxanes, as well as in the modification and silylation of organic compounds and organic polymers. It is known to produce halosilylated hydrocarbon compounds by causing a hydrosilylation reaction between a hydrocarbon compound having an aliphatic unsaturated bond and a hydrogenhalosilane.

It is known, that for the purposes of acceleration and control, such a reaction can be conducted in the presence of oxygen, unsaturated ketone, unsaturated alcohol, tertiary alcohol, ene-yne compound, acetylene alcohol, or acetylene ether (see, e.g. Japanese Unexamined Patent Application Publication [hereinafter referred to as Kokai] H5-213972, Kokai H6-234777, Kokai H8-208838, Kokai H8-231563, Kokai H8-291181, Kokai H9-25281, Kokai H10-29996).

However, the inventor has found that even though a hydrosilylation reaction is conducted between a diene-type compound having vinyl groups on both molecular terminals and a hydrogenhalosilane in the presence of the aforementioned compounds, it is difficult to produce chain hydrocarbons with halosilylated terminal carbon atoms quickly and with improved yield. This is because the process is accompanied by the inevitable formation of by-products in the form of halosilyl group position-changed isomers due to double bond transfer, i.e. by the formation of chain hydrocarbons halosilylated at carbon atoms other than its terminal carbon atoms.

Kokai H9-157276 and Kokai H9-192494 disclose a method wherein 3-chroloropropyltrichlorosilane is produced by subjecting allyl chloride and trichlorosilane to hydrosilylation in the presence of phosphine or tertiary amine. Kokai H11-80167 discloses a method wherein a terminal-silylated polymer is produced by subjecting a polymer with terminal allyl groups and a hydrogenchlorosilane, hydrogenalkoxysilane, or the like, to hydrosilylation in the presence of sulfur.

A disadvantage of the method based on the presence of phosphine or a tertiary amine is that it is unsuitable for selectively halosilylating carbon atoms on terminals of a compound that has vinyl groups on both terminals. A disadvantage of the method based on the presence of sulfur is that sulfur itself may significantly impair activity of a platinum catalyst, so that if it is added in an excessive amount, it will also impair the hydrosilylation reaction. On the other hand, it is not easy to adjust the amount of sulfur to be added to the reaction.

When the chain hydrocarbon halosilylated at its terminal carbon atoms in its initial form or in an alkoxysilylated form obtained by reacting it with an alcohol, is used as a coupling agent, surface-treating agent, or a starting material for modified silicones, it possesses better characteristics than the chain hydrocarbon halosilylated at carbon atoms other than its terminal carbon atoms. Therefore, a demand still exists for a method that would allow production of chain hydrocarbons halosilylated at its terminal carbon atom or its terminal carbon atoms, i.e., a chain hydrocarbon having a halosilyl group at its terminal carbon atom or halosilyl groups at its terminal carbon atoms with higher yield and speed.

SUMMARY OF THE INVENTION

The inventor has arrived at the present invention as a result of a profound study aimed at finding a speedy and high-yield method for the preparation of a chain hydrocarbon halosilylated at a terminal carbon atom or terminal carbon atoms, as well as at finding a hydrosilylation reaction capable of limiting formation of chain hydrocarbons hydrosilylated at carbon atoms other than terminal carbon atoms and formation of by-products in the form of inner double bond transfer isomers. More specifically, it is an object of the present invention to provide a method of high-yield and speedy production of a chain hydrocarbon halosilylated at its terminal carbon atom or terminal carbon atoms that results from hydrosilylation of a diene-type compound having vinyl groups on both molecular terminals and a hydrogenhalosilane. It is another object to provide a hydrosilylation reaction capable of limiting formation of halosilyl-group positional isomers, i.e., chain hydrocarbons halosilylated at carbon atoms other than terminal carbon atoms and by-products in the form of inner double-bond transfer isomers.

The present invention relates to the following;

[1] A method for the preparation of a halosilylated chain hydrocarbon represented by the following formula:

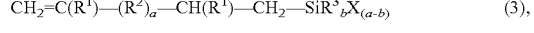

$$CH_2=C(R^1)-(R^2)_a-CH(R^1)-CH_2-SiR^3{}_bX_{(a-b)} \quad (3),$$

or by the following formula:

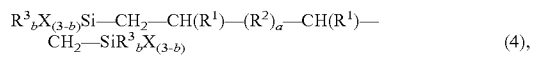

$$R^3{}_bX_{(3-b)}Si-CH_2-CH(R^1)-(R^2)_a-CH(R^1)-$$
$$CH_2-SiR^3{}_bX_{(3-b)} \quad (4),$$

(wherein $R^1$ a hydrogen atom or a monovalent hydrocarbon group, $R^2$ is a divalent hydrocarbon group, $R^3$ is a monovalent saturated hydrocarbon group or an alkoxy group, "a" is 0 or 1 and "b" is an integer from 0 to 2), wherein said halosilylated chain hydrocarbon is produced by subjecting (A) a diene-type compound represented by the following general formula:

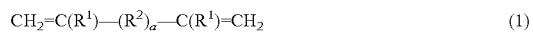

$$CH_2=C(R^1)-(R^2)_a-C(R^1)=CH_2 \quad (1)$$

(wherein $R^1$, $R^2$, and "a" are the same as defined above) and (B) a hydrogenhalosilane represented by the following general formula:

$$HSiR^3{}_bX_{(3-b)} \quad (2)$$

(wherein $R^3$ is a monovalent saturated hydrocarbon group or an alkoxy group, X is a halogen atom, and "b" is an integer from 0 to 2) to a hydrosilylation reaction in the presence of (C) a hydrosilylation catalyst and (D) an ether compound having no aliphatic triple bond.

[2] The method of according to [1], wherein said ether compound (D) is selected from the group consisting of an epoxy compound and compounds represented by the following general formulae:

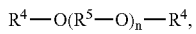 (5)

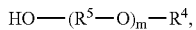 (6)

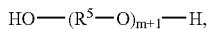 (7)

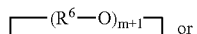 (8) or

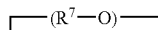 (9)

(wherein $R^4$ is a monovalent saturated hydrocarbon group or a monovalent silylated saturated hydrocarbon group, $R^5$ is a divalent saturated hydrocarbon group or a silylalkyloxyalkylene group, $R^6$ is a divalent hydrocarbon group or a silylalkyloxyalkylene group, $R^7$ is a divalent hydrocarbon having 2 or more carbon atoms; "n" is an integer equal to or greater than 0, and "m" is an integer equal to or greater than 1).

[3] The method according to [1], wherein $R^1$ is a hydrogen atom or an alkyl group and $R^2$ is an alkylene group.

[4] The method according to [1], wherein $R^3$ is an alkyl group, and X is a halogen atom.

[5] The method according to [1], wherein $R^4$ is an alkyl group, $R^5$ is an alkylene group, $R^6$ is an ethylene group or an propylene group, and $R^7$ is any group between ethylene and hexylene, inclusively.

[6] A method of conducting a hydrosilylation reaction, characterized by subjecting (A) a diene-type compound of the following general formula:

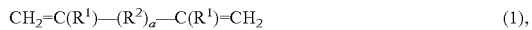 (1), (wherein $R^1$ is a hydrogen atom or a monovalent hydrocarbon group, $R^2$ is a divalent hydrocarbon group, "a" is 0 or 1), and (B) a hydrogenhalosilane represented by the following general formula:

$HSiR^3{}_bX_{(3-b)}$ (2), (wherein $R^3$ is a monovalent saturated hydrocarbon group or an alkoxy group, X is a halogen atom, and "b" is an integer from 0 to 2) to a hydrosilylation reaction in the presence of (C) a hydrosilylation catalyst and (D) an ether compound having no aliphatic triple bond).

[7] The method of conducting a hydrosilylation reaction according to [6], wherein said compound (D) is selected from the group consisting of an epoxy compound and compounds represented by the following general formulae:

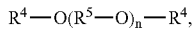 (5)

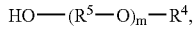 (6)

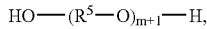 (7)

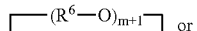 (8) or

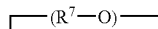 (9)

(wherein $R^4$ is a monovalent saturated hydrocarbon group or a monovalent silylated saturated hydrocarbon group, $R^5$ is a divalent saturated hydrocarbon group or a silylalkyloxyalkylene group, $R^6$ is a divalent hydrocarbon group or a silylalkyloxyalkylene group, $R^7$ is a divalent hydrocarbon having 2 or more carbon atoms; "n" is an integer equal to or greater than 0, and "m" is an integer equal to or greater than 1).

[8] The method of conducting a hydrosilylation reaction according to [6], wherein $R^1$ is a hydrogen atom or an alkyl group and $R^2$ is an alkylene group.

[9] The method of conducting a hydrosilylation reaction according to [6], wherein $R^3$ is an alkyl group, and X is a halogen atom.

[10] The method of conducting a hydrosilylation reaction according to [6], wherein $R^4$ is an alkyl group, $R^5$ is an alkylene group, $R^6$ is an ethylene group or an propylene group, and $R^7$ is any group between ethylene and hexylene, inclusively.

The present invention provides speedy and high-yield production of a chain hydrocarbon halosilylated at its terminal carbon atom or terminal carbon atoms by using a diene-type compound with vinyl groups on both terminals and a hydrogenhalosilane as starting materials. When a diene-type compound and a hydrogenhalosilane are subjected to hydrosilylation reaction by the method of the present invention, it becomes possible to limit formation of halosilyl-group positional isomers, i.e., chain hydrocarbons halosilylated at carbon atoms other than its terminal carbon atoms and by-products in the form of inner double-bond transfer isomers when a diene-type compound having vinyl groups which are not directly bonded to any arylene group is used.

BEST MODE FOR CARRYING OUT THE INVENTION (A) a chain hydrocarbon represented by the following formula:

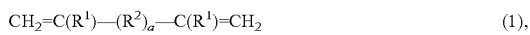 (1), (wherein $R^1$ is a hydrogen atom or a monovalent saturated hydrocarbon group) is one of the main starting materials. Such a monovalent hydrocarbon group may be represented by an alkyl group or an aryl group. The alkyl group may be exemplified by a methyl group, ethyl group, propyl group, hexyl group, and octyl group. The aryl group may be represented by a phenyl group. In one molecule, $R^1$ may be comprised of a combination of a hydrogen atom with one of the aforementioned hydrocarbon groups, or may be comprised of a combination of different monovalent hydrocarbon groups. $R^2$ may be present as a divalent hydrocarbon group, or may be absent at all.

It is recommended that the divalent hydrocarbon group be a divalent saturated hydrocarbon group. Such a group can be represented by an alkylene group, arylene group, or an alkylene-arylene-alkylene group. The divalent hydrocarbon group may also be comprised of an alkenylene group. The alkylene group can be represented by a methylene group, ethylene group, propylene group, butylene group, pentylene group, and a hexylene group. The arylene group can be represented by a phenylene group. The alkylene-arylene-alkylene group can be exemplified by a methylene-phenylene-methylene group. The alkenylene group may be represented by a vinylene group and a methylene-vinylene-methylene group.

"a", may be 0 or 1. Diene-type compounds to have "a" equal to 0 is preferable, and diene-type compounds to have "a" equal to 1 and contain alkylene groups as $R^2$ is also preferable. The alkylene groups have preferably a number of carbon atoms in the range of 1 to 14, and more preferably 1 to 6.

The following are specific examples of the diene-type compound (A): 1,3-butadiene, isoprene, 1,4-pentadiene, 1,5-hexadinene, 1,6-heptadiene, 1,7-octadiene, 1,7-nonadiene, 1,9-decadiene, and 1,17-octadecadiene.

(B) a hydrogenhalosilane represented by the general formula;

$$HSiR^3{}_bX_{(3-b)} \qquad (2)$$

is another one of the main starting materials. A chain hydrocarbon halosilylated at one of its terminal carbon atoms can be obtained by adding its silicon-bonded hydrogen atom and —SiR$^3{}_b$X$_{(3-b)}$ to a vinyl group on one terminal of the diene-type compound (A). Alternatively, a chain hydrocarbon halosilylated at its both terminal carbon atoms can be obtained by adding its silicon-bonded hydrogen atom and —SiR$^3{}_b$X$_{(3-b)}$ to vinyl groups on both molecular terminals of the diene-type compound (A).

In formula (2), R$^3$ may be comprised of a monovalent saturated hydrocarbon group or an alkoxy group. The monovalent saturated hydrocarbon group may be represented by an alkyl group, cycloalkyl group, and an aryl group. The aforementioned alkyl group may be exemplified by a methyl group, ethyl group, propyl group, t-butyl group, and hexyl group. The monovalent saturated hydrocarbon group may be optionally substituted. A halogenated saturated hydrocarbon group may be exemplified by a fluorinated alkyl group, such as a 3,3,3-trifluoropropyl group.

An example of an aryl group is a phenyl group. The alkoxy group can be represented by a methoxy group, ethoxy group, and propoxy group. A monovalent saturated hydrocarbon group and an alkoxy group can be bonded to the same silicon atom of hydrogenhalosilane (B), and different monovalent saturated hydrocarbon groups can be bonded to the same silicon atom of hydrogenhalosilane (B).

X designates a halogen atom, e.g., chlorine. In the above formula (2), "b" is an integer from 0 to 2, inclusively. The following are specific examples of hydrogenhalosilane (B): hydrogentrichlorosilane, ydrogenmethyldichlorosislane, hydrogendimethylchlorosilane, hydrogenethyldichlorosilane, hydrogenphenyldichlorosilane, hydrogenmethoxydichlorosilane, and hydrogenmethylmethoxychlorosilane.

An amount of hydrogenhalosilane (B) required for addition to a vinyl group on one terminal of diene-type compound (A) may be within the range of 0.1 to 1.2 moles, preferably 0.5 to 1.0 mole, per 1 mole of diene-type compound (A). If hydrogenhalosilane (B) is used in an amount below the recommended lower limit, the process will be inefficient, as diene-type compound (A) will become excessive. If, on the other hand, hydrogenhalosilane (B) is used in an amount exceeding the recommended upper limit, the process will have low yield since the adduct to the vinyl groups on both molecular terminals will be produced in excess of the demand.

An amount of hydrogenhalosilane (B) required for addition to vinyl groups on both terminals of diene-type compound (A) may be within the range of 0.5 to 2.2 moles, preferably 1.2 to 2.0 mole per 1 mole of diene-type compound (A). If in the last-mentioned case hydrogenhalosilane (B) is used in an amount below the recommended lower limit, the process will be inefficient, and, if on the other hand, hydrogenhalosilane (B) is used in an amount exceeding the recommended upper limit, the efficiency of the process and yield of the product will decrease because of the excessive amount of hydrogenhalosilane (B).

Hydrosilylation catalyst (C) is a catalyst required of addition of hydrogenhalosilane (B) to diene-type compound (A). The following are specific examples of hydrosilylation catalyst (C): 0-valency platinum-diolefin complex, 0-valency platinum-alkylacetoacetate complex, a complex of 0-valency platinum and 1,3-divinyltetramethyldisiloxane, a halide of a divalent platinum-olefin complex, chloroplatinic acid, a fine-powdered platinum on a carbon carrier, a fine-powdered platinum on a silica carrier, etc. It is understood that such catalysts can be used in combination of two or more.

There are no special restrictions with regard to the amount in which hydrosilylation catalyst (C) can be added, if it is enough to promote the hydrosilylation reaction. It is recommended, however, to add it in an amount of 0.000001 to 1 mole %, preferably 0.0004 to 0.01 mole % based on diene-type compound (A). This is because, if the added amount is below the recommended lower limit, the hydrosilylation reaction will be delayed and have low efficiency. If the added amount exceeds the upper limit, the process will become economically unjustifiable.

An ether compound (D), which has no aliphatic triple bond, is used for promoting addition of —SiR$^3{}_b$X$_{(3-b)}$ preferentially to its terminal carbon atom or terminal carbon atoms of its molecular terminal vinyl group of diene-type compound (A). Ether compound (D), which has no aliphatic triple bond, may be represented by an appropriate ether compound that has no aliphatic unsaturated bond. Typically, such compounds can be selected from the group consisting of epoxy compounds and those exemplified by formulae (5) to (9) given below:

  (5)

  (6)

  (7)

  (8)

  (9)

(wherein R$^4$ is a monovalent saturated hydrocarbon group or a monovalent silylated saturated hydrocarbon group, R$^5$ is a divalent saturated hydrocarbon group or a silylalkyloxyalkylene group, R$^6$ is a divalent hydrocarbon group or a silylalkyloxyalkylene group, R$^7$ is a divalent hydrocarbon having 2 or more carbon atoms; "n" is an integer equal to 0 or greater, and "m" is an integer equal to or greater than 1).

Among possible groups of R$^4$, a monovalent saturated hydrocarbon may be exemplified by an alkyl group, aryl group, and aralkyl group, but the alkyl group is preferable. An alkyl group of R$^4$ may be represented by an ethyl group, propyl group, butyl group, and cyclohexyl group. An aryl group of R$^4$ may be represented by a phenyl group and tolyl group. An aralkyl group of R$^4$ may be represented by a benzyl group and phenethyl group. A monovalent silylated saturated hydrocarbon group may be represented preferably by a silylalkyl group, as well as by a trimethoxysilylether group, triethoxysilylether group, trimethoxysilylpropyl group, triethoxysilylpropyl group, methyldimethoxysilylethyl group, methyldiethoxysilylethyl group, trimethylsilylethyl group, or a similar alkoxysilylalkyl group, alkylalkoxysilylalkyl group, and alkylsilylalkyl group. In one molecule, $R^4$ may be comprised of different monovalent saturated hydrocarbon groups or of a monovalent saturated hydrocarbon group and a silylalkyl group.

$R^5$ is a divalent saturated hydrocarbon group or a silylalkyloxyalkylene group. The divalent saturated hydrocarbon group may be represented by an alkylene group and arylene group, of which the alkylene group is preferable. As an alkylene group, $R^5$ may be represented by an ethylene group, propylene group, butylene group, and pentylene group. As an arylene group, $R^5$ may be represented by a phenylene group. As a silylalkyloxyalkylene group, $R^5$ may be represented by a trimethoxysilylalkyloxyethylene group. In one molecule, $R^5$ may be comprised of different divalent hydrocarbon groups.

$R^6$ is a divalent hydrocarbon group or a silylalkyloxyalkylene group. The divalent hydrocarbon group may be represented by an alkylene group and arylene group, of which the alkylene group is preferable. As an alkylene group, $R^6$ may be represented by a methylene group, ethylene group, butylene group, and pentylene group. As an arylene group, $R^6$ may be represented by a phenylene group and benzylene group. As a silylalkyloxyalkylene group, $R^6$ may be represented by a trimethoxysilylpropyloxyethylene group. In one molecule, $R^6$ may be comprised of different groups.

$R^7$ is a divalent hydrocarbon having 2 or more carbon atoms. Such a divalent hydrocarbon group may be comprised of an alkylene group, arylene group, and alkylene-arylene-alkylene group.

"n" is an integer equal to or greater than 0, and "m" is an integer equal to or greater than 1. It is preferable to have "n" within the range of 0 to 20, and "m" within the range of 1 to 20.

An ether compound (D) may be either liquid at room and reaction temperatures, or may be solid and soluble in below-described solvents. Such an ether compound may be represented by a diethylether, dipropylether, dibutylether, diphenylether, dibenzylether, bis(trimethoxysilylpropyl) ether, ethyleneoxide, propyleneoxide, tetrahydrofuran, tetrahydropyran, dihydrobenzofuran (coumaran), 1,4-dioxane, α,ω-bisethoxypolyethyleneglycol, α-ethoxypolyethylene glycol, α,ω-bis(trimethylsilyl)polyethyleneglycol, polyethyleneglycol, α,ω-bis (methyldimethoxysilylpropyl)polyethyleneglycol, α,ω-bis (methyldimethoxysilylethyl)polyethyleneglycol polypropyleneglycol, 1,2-epoxycyclohaxane, glycidyl alcohol, 3-glycidoxypropyltrimethoxysilane, or mixtures of two or more of the above compounds.

It is recommended to add ether compound (D) to the composition in an amount of 0.01 to 1000 mole %, preferably 0.5 to 20 mole % based on diene-type compound (A). If it is used in a smaller amount, the effect of restricting the formation of isomeric by-products will be insufficient. If the added amount exceeds the upper limit, this will impair the reaction efficiency.

The following description will be related to operation conditions of the inventive method. A halosilylated chain hydrocarbon represented by the following formula:

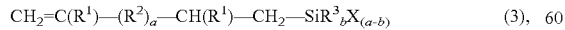  (3), or by the following formula:

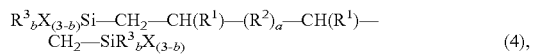  (4), (wherein $R^1$, $R^2$, $R^3$, "a" and "b" are the same as defined above), can be prepared by the following methods;

(1) uniformly mixing aforementioned components (A) through (D) and carrying out a reaction in the atmosphere of inert gas at a temperature of −50° C. to 200° C., preferably 0° C. to 150° C.;

(2) uniformly mixing components (A), (B), and (D) and then loading component (C) and conducting a reaction in the atmosphere of an inert gas at −50° C. to 200° C., preferably 0° C. to 150° C.;

(3) uniformly mixing components (A), (C), and (D) and then loading component (B) dropwise or intermittently and conducting a reaction in the atmosphere of an inert gas at −50° C. to 200° C., preferably 0° C. to 150° C.; or (4) uniformly mixing components (B), (C), and (D) and then loading component (A) dropwise or intermittently and conducting a reaction in the atmosphere of an inert gas at −50° C. to 200° C., preferably 0° C. to 150° C.

The reaction time cannot be defined unequivocally as it will depend on the reaction temperature, activity of the hydrosilylation catalyst, concentration of components, etc., but when the reaction is carried out at room temperature, it may normally last from 12 hours to 7 days, preferably 1 to 3 days. If the reaction is carried out at a temperature of 70 to 150° C., it may last from 5 hours to 1 min., preferably 3 hours to 10 min. When the reaction is carried out in the presence of a platinum-type catalyst with continuous heating of the reaction mixture, the reaction can be completed within 1 min. to 1 sec. In view of low cost of gaseous nitrogen, it s recommended to use it as inert gas for the process.

According to the method of the present invention, the hydrosilylation reaction can be carried out in a solvent, provided that the solvent is used in an amount, which is not detrimental to the hydrosilylation reaction and which is selected from solvents suitable for efficiently dissolving diene-type compound (A), halogenhalosilane (B), and ether compound (D). Preferable solvents are toluene, xylene, benzene, or other aromatic solvents.

If necessary, upon completion of the hydrosilylation reaction, the product can be heated under vacuum for removing unreacted residue of the starting materials. Furthermore, distillation of the reaction product will result in the formation of the target product, i.e., a purer chain hydrocarbon halosilylated at its terminal carbon atom or halosilylated at terminal carbon atoms

EXAMPLES

The present invention will now be described with reference to practical examples.

Analysis of halosilylated hydrocarbons mentioned in practical and comparative examples was performed by gas chromatography with the use of a thermal conductivity detector and by comparing the results with measurements of the same characteristics in standard samples by means of NMR analysis. Reaction efficiency of the hydrogenhalosilane was evaluated with the use of gas chromatography as a percentage of hydrogenhalosilane participated in the reaction versus the loaded amount of hydrogenhalosilane. Polyethyleneglycol #400 is polyethylene having an average molecular weight of 380 to 420 and an average degree of polymerization of 8 to 14.

Practical Examples 1 to 7

A glass reaction vessel filled with gaseous nitrogen was loaded with 2.05 g (0.0250 moles) of 1,5-hexadiene, an ether compound in an amount that provided 5.6% mole of etherified oxygen relative to the aforementioned 1,5-hexadiene, and 0.0050 g of an isopropyl-alcohol solution of chloroplatinic acid (concentration of platinum was 3.6 wt. %). The components were uniformly mixed, additionally combined with 1.70 g (0.0125 moles) of hydrogentrichlorosilane, and mixed again. The reaction vessel was sealed with a cover against leakage of the gaseous nitrogen, the mixture was retained intact for 24 hours at room temperatures (20±5° C.), and the contents in the reaction vessel were subjected to a gas-chromatography analysis. The weight ratio of the produced 5-hexenyltrichlorosilane, 4-hexenyltrichlorosilane, and 1-methyl-4-pentenyltrichlorosilane and the reaction efficiency of the hydrogentrichlorosilane are shown in Table 1.

Comparative Example 1

A glass reaction vessel filled with gaseous nitrogen was loaded with 2.05 g (0.0250 moles) of 1,5-hexadiene and 0.0050 g of an isopropyl-alcohol solution of chloroplatinic acid (concentration of platinum was 3.6 wt. %). The components were uniformly mixed, additionally combined with 1.70 g (0.0125 moles) of hydrogentrichlorosilane, and mixed again. The reaction vessel was sealed with a cover against leakage of the gaseous nitrogen, the mixture was retained intact for 24 hours at room temperatures (20±5° C.), and the contents in the reaction vessel were subjected to a gas-chromatography analysis. The weight ratio of the produced 5-hexenyltrichlorosilane, 4-hexenyltrichlorosilane, and 1-methyl-4-pentenyltrichlorosilane and the reaction efficiency of the hydrogentrichlorosilane are shown in Table 1.

TABLE 1

| | Ether compound | 5-hexehyltrichloro-silane/4-hexenyl-trichlorosilane/1-methyl-4-pentenyl-trichloro-silane | Hydro-gentrichloro-silane reaction efficiency (%) |
|---|---|---|---|
| Comp. Example 1 | None | 54.2/33.8/12.0 | 31.3 |
| Pr. Example 1 | Polyethyleneglycol #400 | 90.1/9.9/0 | >99 |
| Pr. Example 2 | Tetrahydrofuran | 91.1/8.9/0 | 71.3 |
| Pr. Example 3 | Diethyleneglycol-dimethylether | 88.9/10.9/0.2 | >99 |
| Pr. Example 4 | Diethyleneglycol-dibutylether | 89.6/10.1/03 | >99 |
| Pr. Example 5 | 1,4-dioxane | 86.5/10.7/2.8 | 82.2 |
| Pr. Example 6 | Di(n-buityl) ether | 83.1/9.9/7.1 | >99 |
| Pr. Example 7 | Diethylether | 84/5/10.3/5.2 | >99 |

Practical Example 8

A glass reaction vessel filled with gaseous nitrogen was loaded with 5.0 g of toluene and 0.54 g (0.10 mole) of 1,3-butadiene, and components were dissolved. The solution was combined and uniformly mixed with 0.020 g of polyethyleneglycol #400 (used in an amount that provided 4.5 mole % of etherified oxygen relative to the aforementioned 1,3-butadiene) and 0.020 g of an isopropyl-alcohol solution of chloroplatinic acid (concentration of platinum was 3.6 wt. %). The components were then additionally combined and uniformly mixed with 0.68 g (0.0050 moles) of hydrogentrichlorosilane. The reaction vessel was sealed with a cover against leakage of the gaseous nitrogen, the mixture was retained intact for 72 hours at room temperatures (20±5° C.), and the contents in the reaction vessel were subjected to a gas-chromatography analysis. The weight ratio of the produced 3-butenyltrichlorosilane and 2-butenyltrichlorosilane and the reaction efficiency of the hydrogentrichlorosilane are shown in Table 2.

Practical Example 9

A glass reaction vessel filled with gaseous nitrogen was loaded with 5.0 g of tetrahydrofuran and 0.54 g (0.10 mole) of 1,3-butadiene, and components were dissolved. The solution was combined and uniformly mixed with 0.020 g of an isopropyl-alcohol solution of chloroplatinic acid (concentration of platinum was 3.6 wt. %). The components were then additionally combined and uniformly mixed with 0.68 g (0.0050 moles) of hydrogentrichlorosilane. The reaction vessel was sealed with a cover against leakage of the gaseous nitrogen; the mixture was retained intact for 72 hours at room temperatures (20±5° C.), and the contents in the reaction vessel were subjected to a gas-chromatography analysis. The weight ratio of the produced 3-butenyltrichlorosilane and 2-butenyl-trichlorosilane and the reaction efficiency of the hydrogen-trichlorosilane are shown in Table 2.

Comparative Example 2

A glass reaction vessel filled with gaseous nitrogen was loaded with 5.0 g of toluene and 0.54 g (0.10 mole) of 1,3-butadiene, and components were dissolved. The solution was combined and uniformly mixed with 0.02 g of an isopropyl-alcohol solution of chloroplatinic acid (concentration of platinum was 3.6 wt. %). The components were then additionally combined and uniformly mixed with 0.68 g (0.0050 moles) of hydrogentrichlorosilane. The reaction vessel was sealed with a cover against leakage of the gaseous nitrogen, the mixture was retained intact for 72 hours at room temperatures (20±5° C.), and the contents in the reaction vessel were subjected to a gas-chromatography analysis. The weight ratio of the produced 3-butenyltrichlorosilane and 2-butenyltrichlorosilane and the reaction efficiency of the hydrogentrichlorosilane are shown in Table 2.

TABLE 2

| | Ether compound | 3-butenyltrichlorosilane/ 2-butenyltrichlorosilane | Hydrogentrichlorosilane reaction efficiency (%) |
|---|---|---|---|
| Comp. Example 2 | None | Product was not obtained | 0 |
| Pr. Example 8 | Polyethyleneglycol #400 | 69.6/30.4 | 60.0 |
| Pr. Example9 | Tetrahydrofuran | 58.6/41.4 | >99 |

Practical Example 10

A glass reaction vessel filled with gaseous nitrogen was loaded with 3.45 g (0.0250 mole) of 1.9-decadiene, a polyethyleneglycol #400 used in an amount that provided 5.6 mole % of etherified oxygen relative to the aforementioned 1,9-decadiene, and 0.0050 g of an isopropyl-alcohol solution of chloroplatinic acid (concentration of platinum was 3.6 wt. %). The components were then additionally combined and uniformly mixed with 1.70 g (0.0125 moles) of hydrogentrichlorosilane. The reaction vessel was sealed with a cover against leakage of the gaseous nitrogen, the mixture was retained intact for 24 hours at room temperatures (20±5° C.), and the contents in the reaction vessel were subjected to a gas-chromatography analysis. The weight ratio of the produced 9-decenyltrichlorosilane and 8-decenyltrichlorosilane and the reaction efficiency of the hydrogentrichlorosilane are shown in Table 3.

Comparative Example 3

A glass reaction vessel filled with gaseous nitrogen was loaded with 3.45 g (0.0250 mole) of 1,9-decadiene and 0.0050 g of an isopropyl-alcohol solution of chloroplatinic acid (concentration of platinum was 3.6 wt. %). The components were then mixed and additionally combined with 1.70 g (0.0125 moles) of hydrogentrichlorosilane. The reaction vessel was sealed with a cover against leakage of the gaseous nitrogen; the mixture was retained intact for 24 hours at room temperatures (20±5° C.), and the contents in the reaction vessel were subjected to a gas-chromatography analysis. The weight ratio of the produced 9-decenyltrichlorosilane and 8-decenyltrichlorosilane and the reaction efficiency of the hydrogentrichlorosilane are shown in Table 3.

ylenglycol #400 used in an amount that provided 5.6 mole % of etherified oxygen relative to the aforementioned 1,5-hexadiene, and 0.0050 g of an isopropyl-alcohol solution of chloroplatinic acid (concentration of platinum was 3.6 wt. %). The components were then additionally combined and uniformly mixed with 1.44 g (0.0125 moles) of hydrogenmethyldichlorosilane. The reaction vessel was sealed with a cover against leakage of the gaseous nitrogen, the mixture was retained intact for 24 hours at room temperatures (20±5° C.), and the contents in the reaction vessel were subjected to a gas-chromatography analysis. The weight ratio of the produced 5-hexenylmethyldichlorosilane and 4-hexenylmethyldichlorosilane and the reaction efficiency of the hydrogenmethyldichlorosilane are shown in Table 4.

Comparative Example 4

A glass reaction vessel filled with gaseous nitrogen was loaded with 2.05 g (0.0250 mole) of 1.5-hexadiene and 0.0050 g of an isopropyl-alcohol solution of chloroplatinic acid (concentration of platinum was 3.6 wt. %). The components were then additionally combined and uniformly mixed with 1.44 g (0.0125 moles) of hydrogenmethyldichlorosilane. The reaction vessel was sealed with a cover against leakage of the gaseous nitrogen, the mixture was retained intact for 24 hours at room temperatures (20±5° C.), and the contents in the reaction vessel were subjected to a gas-chromatography analysis. The weight ratio of the produced 5-hex-

TABLE 3

|  | Ether compound | 9-decenyltrichlorosilane/ 8-decenyltrichlorosilane | Hydrogetrichlorosilane reaction efficiency (%) |
|---|---|---|---|
| Comp. Example 3 | None | 88.8/11.2 | >99 |
| Pr. Example 10 | Polyethyleneglycol #400 | 91.0/9.0 | >99 |

Practical Example 11

A glass reaction vessel filled with gaseous nitrogen was loaded with 2.05 g (0.0250 mole) of 1.5-hexadiene, polyethenylmethyldichlorosilane, 4-hexenylmethyldichlorosilane, and 1-methyl-4-pentenylmethyldichlorosilane and the reaction efficiency of the hydrogenmethyldichlorosilane are shown in Table 4.

TABLE 4

|  | Ether compound | 5-hexenylmethyldichlorosilane/ 4-hexenylmethyldichlorosilane/ 1-methyl-4-pentenylmethyldichlorosilane | Hydrogenmethyldichlorosilane reaction efficiency (%) |
|---|---|---|---|
| Comp. Example 4 | None | 81/0/18.0/1.0 | >99 |
| Pr. Example 11 | Polyethyleneglycol #400 | 91.5/7.8/0.7 | >99 |

Practical Examples 12 to 15

A 200 ml four-neck flask filled with nitrogen and equipped with a reflux condenser was loaded with 41.0 g (0.50 mole) of 1,5-hexadiene, an ether compound used in an amount that provided 5.6 mole % of etherified oxygen relative to the aforementioned 1,5-hexadiene, and 0.18 g of an isopropyl-alcohol solution of chloroplatinic acid (concentration of platinum was 3.6 wt. %). The components were uniformly mixed, heated to 50° C., and additionally combined with 135.5 g (1.00 mole) of hydrogentrichlorosilane added dropwise. Upon completion of the addition, the mixture was aged for 1 hour at 120° C. and then cooled. The contents in the flask were subjected to a gas-chromatography analysis. The weight ratio of the produced 1,6-bis(trichlorosilyl)hexane, 1,5-bis(trichlorosilyl)hexane, and 2,5-bis(trichlorosilyl)hexane and the reaction efficiency of the hydrogentrichlorosilane are shown in Table 5.

Comparative Example 5

A 200 ml four-neck flask filled with nitrogen and equipped with a reflux condenser was loaded with 41.0 g (0.50 mole) of 1,5-hexadiene and 0.18 g of an isopropyl-alcohol solution of chloroplatinic acid (concentration of platinum was 3.6 wt. %). The components were uniformly mixed, heated to 50° C., and additionally combined with 135.5 g (1.00 mole) of hydrogentrichlorosilane added dropwise. Upon completion of the addition, the mixture was aged for 1 hour at 120° C. and then cooled. The contents in the flask were subjected to a gas-chromatography analysis. The weight ratio of the produced 1,6-bis (trichlorosilyl)hexane, 1,5-bis(trichlorosilyl)hexane, and 2,5-bis(trichlorosilyl) hexane and the reaction efficiency of the hydrogentrichlorosilane are shown in Table 5.

TABLE 5

| | Ether compound | 1,6-bis (trichlorosilyl) hexane/1,5-bis (trichlorosilyl) hexane/2,5-bis (trichlorosilyl) hexane | Hydro-gentrichloro-silane reaction efficiency (%) |
|---|---|---|---|
| Comp. Example 5 | None | 87.9/7.6/4.5 | 88.4 |
| Pr. Example 12 | Polyethyleneglycol #400 | 99.7/0.3/0 | >99 |
| Pr. Example 13 | Tetrahydrofuran | 97.9/1.8/0.3 | >99 |
| Pr. Example 14 | Diethyleneglycol dibutylether | 98.4/1.5/0.1 | >99 |
| Pr. Example 15 | 3-glycidoxypropyl trimethoxysilane | 99.5/0.5/0 | >99 |

Practical Example 16

A 200 ml four-neck flask filled with gaseous nitrogen and equipped with a reflux condenser was loaded with 12.6 g (0.185 mole) of isoprene, polyethyleneglycol #400 used in an amount that provided 5.6 mole % of etherified oxygen relative to the aforementioned 1,5-hexadiene, and 0.060 g of an iso-propyl-alcohol solution of chloroplatinic acid (concentration of platinum was 3.6 wt. %). The components were uniformly mixed, heated to 30° C., and additionally combined with 50.2 g (0.370 mole) of hydrogentrichlorosilane added dropwise. Upon completion of the addition, the mixture was aged for 1 hour at 80° C. and then cooled. The contents in the flask were subjected to a gas-chromatography analysis. The weight ratio of the produced 1,4-bis (trichlorosilyl)-2-methylbutane and 1,3-bis(trichlorosilyl)-2-methylbutane and the reaction efficiency of the hydrogenmethyldichlorosilane are shown in Table 6.

Comparative Example 6

A 200 ml four-neck flask filled with gaseous nitrogen and equipped with a reflux condenser was loaded with 12.6 g (0.185 mole) of isoprene and 0.060 g of an isopropyl-alcohol solution of chloroplatinic acid (concentration of platinum was 3.6 wt. %). The components were uniformly mixed, heated to 30° C., and additionally combined with 50.2 g (0.370 mole) of hydrogentrichlorosilane added dropwise. Upon completion of the addition, the mixture was aged for 1 hour at 80° C. and then cooled. The contents in the flask were subjected to a gas-chromatography analysis. The weight ratio of the produced 1,4-bis (trichlorosilyl)-2-methylbutane and 1,3-bis(trichlorosilyl)-3-methylbutane and the reaction efficiency of the hydrogentrichlorosilane are shown in Table 6.

TABLE 6

| | Ether compound | 1,4-bis (trichlorosilyl)-2-methylbutane/1,3-bis (trichlorosilyl)-3-methylbutane | Hydro-gentrichloro-silane reaction efficiency (%) |
|---|---|---|---|
| Comp. Example 6 | None | 99.5/0.5 | 43.9 |
| Pr. Example 16 | Polyethyleneglycol #400 | 99.8/0.2 | 93.8 |

INDUSTRIAL APPLICABILITY

The preparation method of the present invention is useful for industrially producing chain hydrocarbons halosilylated at its terminal carbon atom or its terminal carbon atoms, i.e., a chain hydrocarbon having a halosilyl group at its terminal carbon atom or halosilyl groups at its terminal carbon atoms with higher yield and speed.

The method of conducting a hydrosilylation reaction of the present invention is useful for industrially producing chain hydrocarbons halosilylated at its terminal carbon atom or its terminal carbon atoms.

The invention claimed is:

1. A method for the preparation of a halosilylated chain hydrocarbon represented by the following formula:

$$CH_2=C(R^1)-(R^2)_a-CH(R^1)-CH_2-SiR^3{}_bX_{(a-b)} \quad (3),$$

or by the following formula:

$$R^3{}_bX_{(3-b)}Si-CH_2-CH(R^1)-(R^2)_a-CH(R^1)-CH_2-SiR^3{}_bX_{(3-b)} \quad (4),$$

wherein $R^1$ is a hydrogen atom or a monovalent hydrocarbon group, $R^2$ is a divalent hydrocarbon group, $R^3$ is a monovalent saturated hydrocarbon group or an alkoxy group, "a" is 0 or 1 and "b" is an integer from 0 to 2, wherein said halosilylated chain hydrocarbon is produced by subjecting (A) a diene-type compound represented by the following general formula:

$$CH_2=C(R^1)-(R^2)_a-C(R^1)=CH_2 \quad (1)$$

wherein $R^1$, $R^2$, and "a" are the same as defined above and (B) a hydrogenhalosilane represented by the following general formula:

$$HSiR^3{}_bX_{(3-b)} \quad (2)$$

wherein $R^3$ is a monovalent saturated hydrocarbon group or an alkoxy group, X is a halogen atom, and "b" is an integer from 0 to 2, to a hydrosilylation reaction in the presence of (C) a hydrosilylation catalyst and (D) an ether compound having no aliphatic triple bond.

2. The method of according to claim 1, wherein said ether compound (D) is selected from the group consisting of an epoxy compound and compounds represented by the following general formulae:

(5)

(6)

(7)

, or
(8)

(9)

wherein $R^4$ is a monovalent saturated hydrocarbon group or a monovalent silylated saturated hydrocarbon group, $R^5$ is a divalent saturated hydrocarbon group or a silylalkyloxyalkylene group, $R^6$ is a divalent hydrocarbon group or a silylalkyloxyalkylene group, $R^7$ is a divalent hydrocarbon having 2 or more carbon atoms; "n" is an integer equal to or greater than 0, and "m" is an integer equal to or greater than 1.

3. The method according to claim 1, wherein $R^1$ is a hydrogen atom or an alkyl group and wherein $R^2$ an alkylene group.

4. The method according to claim 1, wherein $R^3$ is an alkyl group, and X is a halogen atom.

5. The method according to claim 1, wherein $R^4$ an alkyl group, $R^5$ is an alkylene group, $R^6$ is an ethylene group or an propylene group, and $R^7$ is any group between ethylene and hexylene, inclusively.

6. A method of conducting a hydrosilylation reaction, characterized by subjecting (A) a diene-type compound of the following general formula:

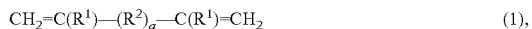
(1), wherein $R^1$ is a hydrogen atom or a monovalent hydrocarbon group, $R^2$ is a divalent hydrocarbon group, "a" is 0 or 1, and (B) a hydrogenhalosilane represented by the following general formula:

(2), wherein $R^3$ is a monovalent saturated hydrocarbon group or an alkoxy group, X is a halogen atom, and "b" is an integer from 0 to 2, to a hydrosilylation reaction in the presence of (C) a hydrosilylation catalyst and (D) an ether compound having no aliphatic triple bond.

7. The method of conducting a hydrosilylation reaction according to claim 6, wherein said compound (D) is selected from the group consisting of an epoxy compound and compounds represented by the following general formulae:

(5)

(6)

(7)

, or
(8)

(9)

wherein $R^4$ is a monovalent saturated hydrocarbon group or a monovalent silylated saturated hydrocarbon group, $R^5$ is a divalent saturated hydrocarbon group or a silylalkyloxyalkylene group, $R^6$ is a divalent hydrocarbon group or a silylalkyloxyalkylene group, $R^7$ is a divalent hydrocarbon having 2 or more carbon atoms; "n" is an integer equal to or greater than 0, and "m" is an integer equal to or greater than 1.

8. The method of conducting a hydrosilylation reaction according to claim 6, wherein $R^1$ a hydrogen atom or an alkyl group and $R^2$ an alkylene group.

9. The method of conducting a hydrosilylation reaction according to claim 6, wherein $R^3$ an alkyl group, and X is a halogen atom.

10. The method of conducting a hydrosilylation reaction according to claim 6, wherein $R^4$ is an alkyl group, $R^5$ is an alkylene group, $R^6$ is an ethylene group or an propylene group, and $R^7$ is any group between ethylene and hexylene, inclusively.

* * * * *